United States Patent [19]

Zaiger

[11] Plant 4,338

[45] Dec. 5, 1978

[54] PLUMCOT TREE

[76] Inventor: C. Floyd Zaiger, 537 Rosemore Ave., Modesto, Calif. 95351

[21] Appl. No.: 862,632

[22] Filed: Dec. 20, 1977

[51] Int. Cl.[2] ..... A01H 5/03

[52] U.S. Cl. ..... Plt./38

[58] Field of Search ..... Plt./33, 38, 39

*Primary Examiner*—Robert E. Bagwill

*Assistant Examiner*—James R. Feyrer

[57] ABSTRACT

This variety relates to an plumcot tree (plum × apricot) which is of medium to large size, medium vigorous, medium dense and slightly spreading in growth; the tree being a regular and productive bearer of medium size, early ripening, firm, freestone fruit with good flavor and shipping quality.

4 Drawing Figures

ORIGIN OF THE VARIETY

The present variety of plumcot tree was originated by me in my experimental orchard, located near Modesto, Stanislaus County, Calif., as a selected seedling from a large number of seedlings obtained from Beauty Plum seeds (unpatented) that resulted from open-pollinated flowers. These seedlings were grown under careful observation by me, gave many and varying characteristics. One such seedling which is the present variety of plumcot tree having been especially desirable as to novel characteristics of fruit. I propagated the variety in anticipation of ultimate introduction to the industry.

ASEXUAL REPRODUCTION OF THE VARIETY

The present variety of plumcot tree was asexually reproduced by me in my experimental orchard by budding and all reproductions run true to the original tree in all respects.

SUMMARY OF THE VARIETY

The present variety of plumcot tree, (plum × apricot) is of medium to large size, medium dense, slightly spreading in growth and a productive and regular bearer of medium size, firm, early ripening, freestone fruit having mottled, yellow-red flesh and red skin color.

The present variety of plumcot tree is further characterized by fruit with a soft down covering similar to an apricot. A pronounced aroma, predominantly apricot but suggestive of plum, with uniform ripening and good eating quality.

BRIEF DESCRIPTION OF THE DRAWING

The accompanying photographs show typical specimens of the foliage and fruit of my new variety with upper and lower surfaces of the foliage being illustrated, also an exterior and a sectional view of the fruit with the stone remaining in place therein. A section of a branch is shown illustration the heavy spurring which causes the medium dense characteristic of the tree. The illustrations were taken shortly after being picked at maturity (shipping ripe) and the colors are as nearly true as reasonably possible in a color representation of this type.

DESCRIPTION OF THE VARIETY

The botanical details of this new and distinct variety of plumcot tree (plum × apricot) with color definitions (except those in common color terms) referenced to Reinhold Color Atlas by A. Korneruf and J. H. Wanscher, are as follows:

Tree:
- *Size.*—Medium to large.
- *Vigor.*—Medium vigorous.
- *Density.*—Medium dense.
- *Shape.*—Slightly spreading — nearly round in silhouette.
- *Production.*—Productive.
- *Bearing.*—Regular.

Trunk:
- *Size.*—Medium stocky.
- *Texture.*—Shaggy.

Branches:
- *Size.*—Medium.
- *Texture.*—Medium rough.
- *Color.*—New growth — Reddish brown. Old growth — Brown to grayish brown.
- *Lenticels.*—Number — Medium.

Leaves:
- *Size.*—Medium. Average length 2½". Average width 1¾".
- *Shape.*—Some elliptical. Many oblanceolate.
- *Thickness.*—Medium.
- *Margin.*—Serrate.
- *Petiole.*—Average length 7/8". Medium thickness.
- *Glands.*—Average number two. Positioned mainly on petiole. Sometimes on base of leaf blade.
- *Color.*—Upper surface — dark green (27-F-4 to 28-F-7). Lower surface — dull green (26-E-4 to 27-E-3).

Flower buds:
- *Size.*—Medium to small.
- *Length.*—Short.
- *Shape.*—Medium to short. Plump.

Flowers:
- *Blooming period.*—Feb. 26, 1977 to Mar. 8, 1977. Varies from year to year due to weather variation.
- *Size.*—Medium to small.
- *Color.*—White — faint tinge of pink.
- *Pistil.*—Pubescent.

Fruit:
- *Maturity when described.*—Firm ripe.
- *Date of first picking.*—June 3, 1977.
- *Date of last picking.*—June 10, 1977.

*Size.*—Small to medium. Average diameter axially 1½". Average transversely in suture plane 1½".

*Form.*—Uniform. Symmetrical. Globose.

*Suture.*—Usually deep and pronounced at stem end and becoming more shallow gradually toward the blossom end. Terminates at blossom end.

*Ventral surface.*—Rounded, some fruits slightly lipped at stem end.

*Apex.*—Flat to slightly rounded. Pistil point slightly depressed.

*Cavity.*—Circular. Average depth — 3/16". Average breadth — ¼".

*Base.*—Truncate.

Skin:

*Thickness.*—Medium.

*Texture.*—Medium. Tenacious to flesh.

*Down.*—Scant. Very short.

*Tendency to crack.*—None.

*Color.*—Bright yellow ground color (5-A-8). Nearly complete overspread with light red (10-A-7) to (10-A-8).

Flesh:

*Color.*—Slightly marbled. Chrome yellow (5-A-8) to geranium red (11-B-7).

*Texture.*—Firm. Fine. Melting.

*Juice.*—Moderate.

*Fibers.*—Medium size.

*Ripens.*—Even.

*Flavor.*—Mild when fully ripe. Slightly tart when hard ripe. Intermediate between plum and apricot.

*Aroma.*—Pronounced.

*Eating quality.*—Good to excellent.

Stone:

*Type.*—Free; adheres to flesh somewhat along ventricle edge.

*Size.*—Medium. Average length — ¾". Average width — 11/16". Average thickness — ⅜".

*Form.*—Ovoid. Slightly cuneate toward apex.

*Base.*—Oblique.

*Tendency to split.*—None.

*Apex.*—Slightly acuminate.

*Surface.*—Regularly pitted, only slightly throughout.

*Wing.*—Sharp wing along ventral edge.

Use: Culinary. Dessert. Home and local market.

Keeping quality: Good.

Shipping quality: Good.

The plumcot tree and its fruit herein described may vary in slight detail due to climatic and soil conditions under which the variety may be grown; the present description being of the variety as grown near Modesto, Stanislaus County, Calif.

I claim:

1. A new and distinct variety of plumcot tree (plum × apricot) substantially as illustrated and described, which bears medium, firm, freestone fruit having mottled yellow-red flesh and a red exterior color; said fruit has a soft down covering similar to an apricot and a pronounced aroma which is predominantly apricot but suggestive of plum, the fruit is further characterized by early ripening and good eating quality.

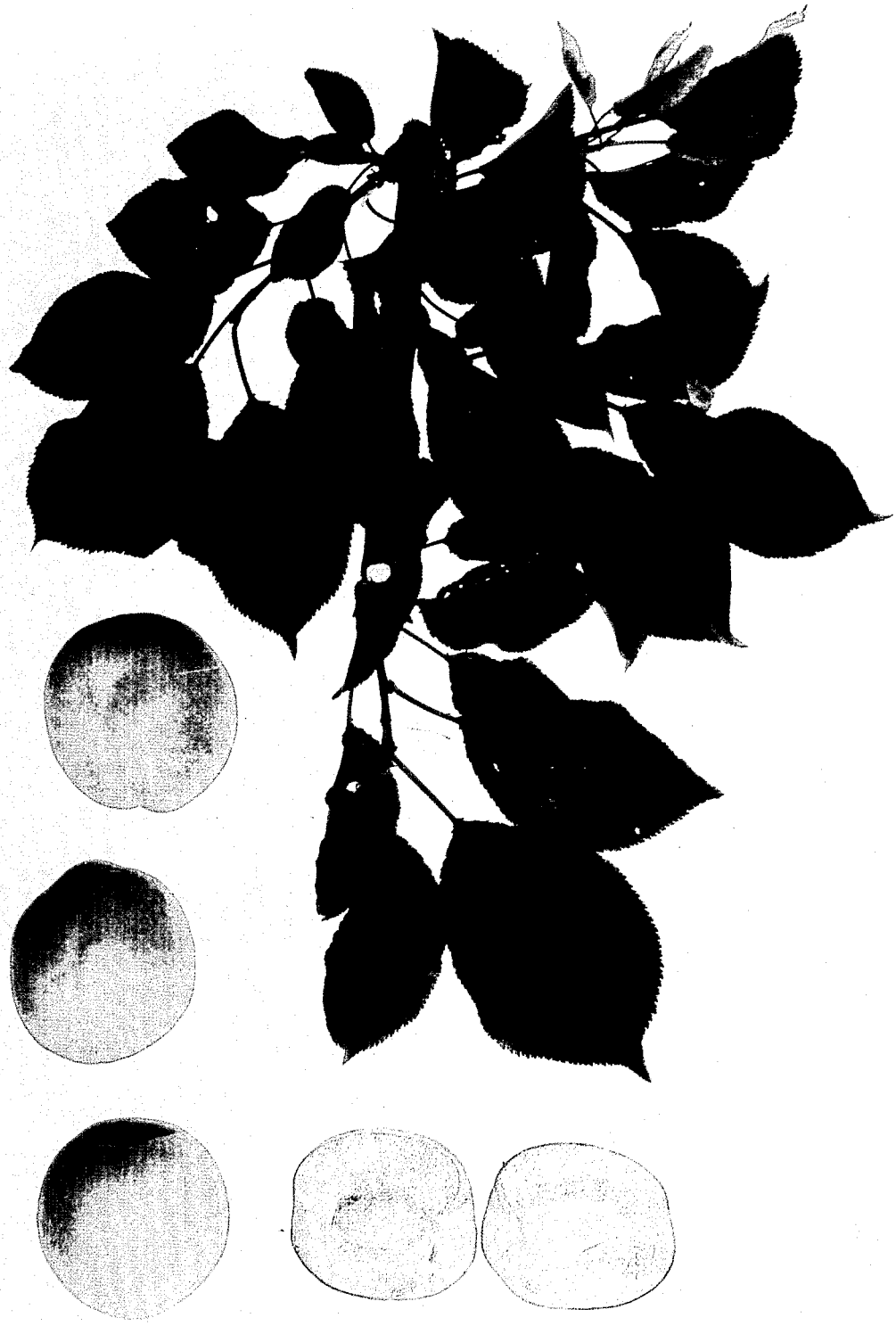

* * * * *